(12) United States Patent
Ho et al.

(10) Patent No.: US 8,989,834 B2
(45) Date of Patent: Mar. 24, 2015

(54) WEARABLE DEVICE

(71) Applicant: Google Inc., Mountain View, CA (US)

(72) Inventors: Harvey Ho, Mountain View, CA (US); Babak Amirparviz, Mountain View, CA (US)

(73) Assignee: Google Inc., Mountain View, CA (US)

( * ) Notice: Subject to any disclaimer, the term of this patent is extended or adjusted under 35 U.S.C. 154(b) by 242 days.

(21) Appl. No.: 13/626,603

(22) Filed: Sep. 25, 2012

(65) Prior Publication Data

US 2014/0085602 A1 Mar. 27, 2014

(51) Int. Cl.
*A61B 5/04* (2006.01)
*A61B 3/10* (2006.01)
*G02C 7/04* (2006.01)
*A61B 5/00* (2006.01)
*A61B 5/053* (2006.01)

(52) U.S. Cl.
CPC . *G02C 7/04* (2013.01); *A61B 3/101* (2013.01); *A61B 5/002* (2013.01); *A61B 5/0537* (2013.01); *A61B 5/6821* (2013.01); *A61B 2560/0412* (2013.01); *A61B 2562/164* (2013.01)
USPC .......................................................... 600/381

(58) Field of Classification Search
CPC ............................ G02C 7/04; B29D 11/00826
See application file for complete search history.

(56) References Cited

U.S. PATENT DOCUMENTS

| | | | |
|---|---|---|---|
| 3,958,560 A | 5/1976 | March | |
| 4,014,321 A | 3/1977 | March | |
| 4,055,378 A | 10/1977 | Feneberg et al. | |
| 4,122,942 A | 10/1978 | Wolfson | |
| 4,136,250 A | 1/1979 | Mueller et al. | |
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |
| 4,604,479 A | 8/1986 | Ellis | |
| 4,632,844 A | 12/1986 | Yanagihara et al. | |

(Continued)

FOREIGN PATENT DOCUMENTS

| | | |
|---|---|---|
| EP | 0369942 | 5/1990 |
| EP | 686372 | 12/1995 |

(Continued)

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

(Continued)

*Primary Examiner* — Max Hindenburg
*Assistant Examiner* — Renee Danega
(74) *Attorney, Agent, or Firm* — McDonnell Boehnen Hulbert & Berghoff LLP

(57) ABSTRACT

Apparatus, systems and methods employing a contact lens that generates information indicative of a hydration level of an eye in which the lens is worn, are provided. In some aspects, a contact lens includes a substrate that forms at least part of a body of the contact lens and a hydration component that generates information associated with a hydration level of an eye in which the contact lens is worn.

24 Claims, 9 Drawing Sheets

(56) References Cited

U.S. PATENT DOCUMENTS

| | | |
|---|---|---|
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint |
| 5,177,165 A | 1/1993 | Valint et al. |
| 5,177,168 A | 1/1993 | Baron |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,145,736 A | 11/2000 | Ours et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1* | 1/2007 | Abreu .......................... 600/475 |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1* | 3/2009 | Sit et al. ........................ 600/398 |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1* | 4/2010 | Amirparviz et al. ......... 351/158 |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |
| 2012/0078071 A1 | 3/2012 | Bohm et al. |
| 2012/0088258 A1 | 4/2012 | Bishop et al. |
| 2012/0092612 A1 | 4/2012 | Binder |
| 2012/0109296 A1 | 5/2012 | Fan |
| 2012/0177576 A1 | 7/2012 | Hu |
| 2012/0201755 A1 | 8/2012 | Rozakis et al. |

(56) References Cited

U.S. PATENT DOCUMENTS

| | | |
|---|---|---|
| 2012/0206691 A1 | 8/2012 | Iwai |
| 2012/0245444 A1 | 9/2012 | Otis et al. |
| 2012/0259188 A1 | 10/2012 | Besling |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| JP | 2003-195230 | 7/2003 |
| WO | 9504609 | 2/1995 |
| WO | 0116641 | 3/2001 |
| WO | 2001034312 | 5/2001 |
| WO | 03065876 | 8/2003 |
| WO | 2004060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," MEMS 2008. IEEE 21st International Conference on. IEEE, 2008., pp. 403-406.
Lähdesmäki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.
Shum et al., "Functional modular contact lens," Proc. of SPIE, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.
Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.
Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Bionic contact lens 'To project emails before eyes,' http://www.kurzweilai.net/forums/topic/bionic-contact-lens-to-project-emails-before-eyes, Last accessed Mar. 14, 2012, 2 pages.
Tweedie, et al., "Contact creep compliance of viscoelastic materials via nanoindentation," J. Mater. Res., Jun. 2006, vol. 21, No. 2, pp. 1576-1589, Materials Research Society.
Brahim, et al., "Polypyrrole-hydrogel composites for the construction of clinically important biosensors," 2002, Biosensors & Bioelectronics, vol. 17, pp. 53-59.
Huang, et al., "Wrinkling of Ultrathin Polymer Films," Mater. Res. Soc. Symp. Proc., 2006, vol. 924, 6 pages, Materials Research Society.
Zarbin, et al., "Nanotechnology in ophthalmology," Can J Ophthalmol, 2010, vol. 45, No. 5, pp. 457-476.
Selner, et al., "Novel Contact Lens Electrode Array for Multi-electrode Electroretinography (meERG)," IEEE, 2011, 2 pages.
Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.
Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.
Pandey, et al., "A Fully Integrated RF-Powered Contact Lens With a Single Element Display," IEEE Transactions On Biomedical Circuits and Systems, Dec. 2010, vol. 4, No. 6, pages.
Lingley, et al., "Multipurpose integrated active contact lenses," SPIE, 2009, 2 pages.
Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3µW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Baxter, "Capacitive Sensors," 2000, 17 pages.

(56) References Cited

OTHER PUBLICATIONS

Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
Unpublished U.S. Appl. No. 13/240,994, Titled "See-Through Display With Infrared Eye-Tracker," Filed Sep. 22, 2011, 38 pages.
Unpublished U.S. Appl. No. 13/209,706, Titled "Optical Display System and Method with Gaze Tracking," filed Aug. 15, 2011, 30 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.
Quick, "Color-changing electrochromic lens technology has fashion and military applications," Gizmag, Jul. 12, 2011, http://www.gizmag.com/electrochromic-lens-technology/19191/, Last accessed Apr. 12, 2012, 4 pages.
Chu, "Contact Lenses that Respond to Light," Technology Review, Nov. 10, 2009, http://www.technologyreview.com/printer_friendly_article_aspx?id=23922, Last accessed Apr. 12, 2012, 2 pages.

* cited by examiner

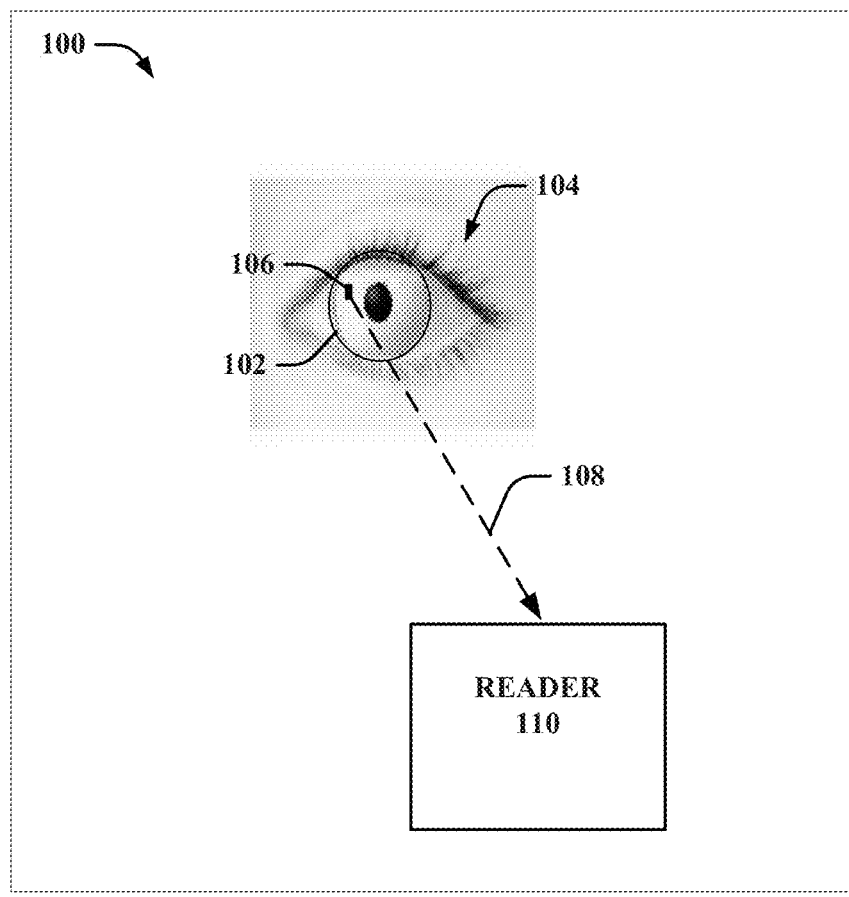
FIG. 1A
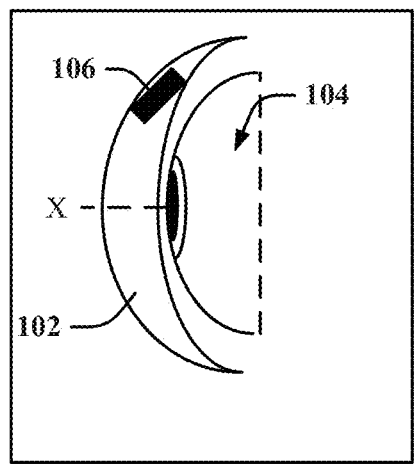 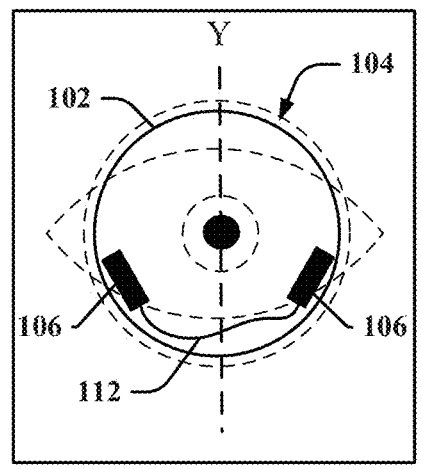
FIG. 1B          FIG. 1C

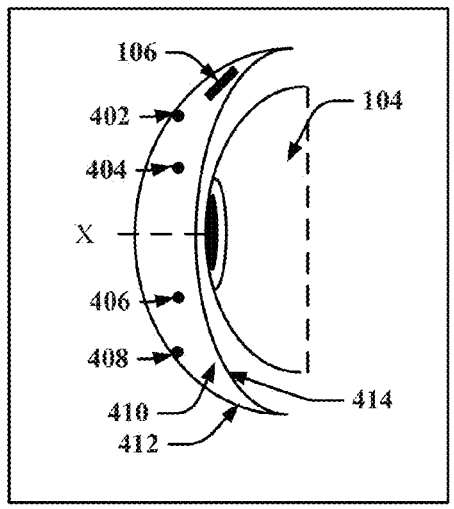 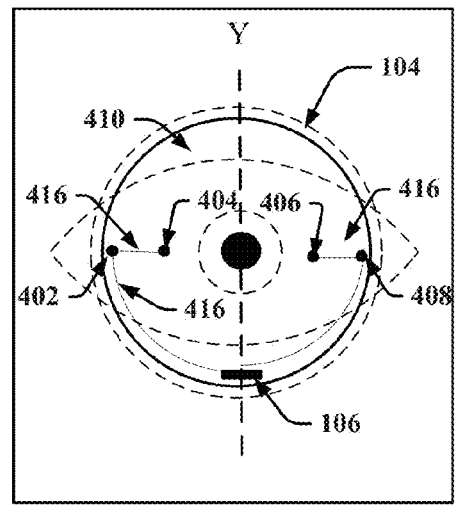
FIG. 4A  FIG. 4B
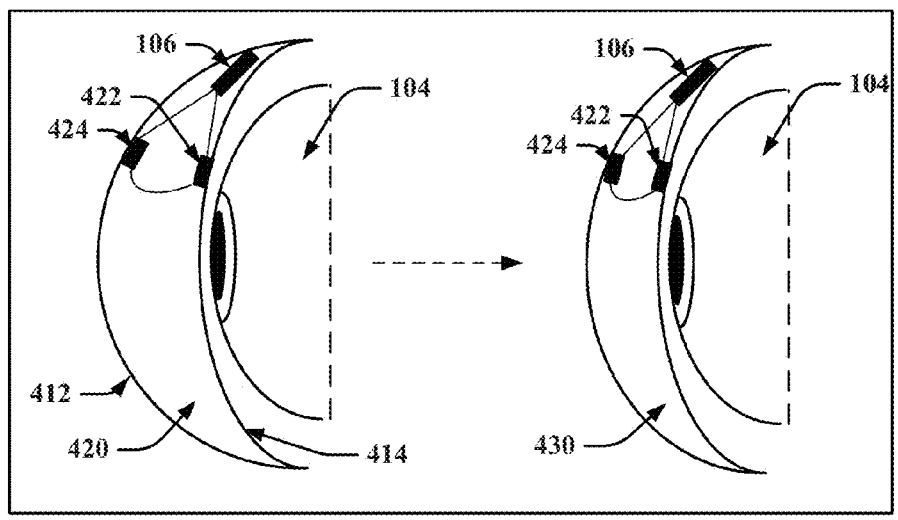
FIG. 4C

WEARABLE DEVICE

TECHNICAL FIELD

This disclosure generally relates to measuring and reporting eye hydration levels via a contact lens.

BACKGROUND

Tears keep the delicate surface of an eyeball clean and wet. Tears are produced in glands above an outer corner of the eye, and they spread across the eye surface with each blink and form a layer of moisture, or tear film, that serves as a protective coat for lubricating the eye and washing away foreign bodies that might cause harm or obscure vision. Tears that wash across the eye naturally evaporate into air or drain into tear ducts. Normally, the eye constantly bathes itself in tears by producing tears at a slow and steady rate so that the eye remains moist and comfortable. However, many people that wear contact lenses or have dry eyes in general may need to apply tear drops to keep their eyes properly hydrated. Yet those individuals may go about the day without knowing that their eyes are too dry or not optimally hydrated with tear fluid.

BRIEF DESCRIPTION OF THE DRAWINGS

FIG. 1A is an illustration of an exemplary non-limiting system that includes a contact lens employing a hydration component to generate information indicative of a hydration level of an eye on/in which the contact lens is worn in accordance with aspects described herein.

FIGS. 1B and 1C depict enlarged perspectives of an example contact lens in accordance with aspects described herein.

FIGS. 4A and 4B depict different perspectives of an example contact lens having a four point detection probe for generating information indicative of a hydration level of an eye on/in which the contact lens is worn in accordance with aspects described herein.

FIG. 4C depicts an example contact lens having sensors for generating information indicative of a hydration level of an eye on/in which the contact lens is worn in accordance with aspects described herein.

DETAILED DESCRIPTION

Figure 2:
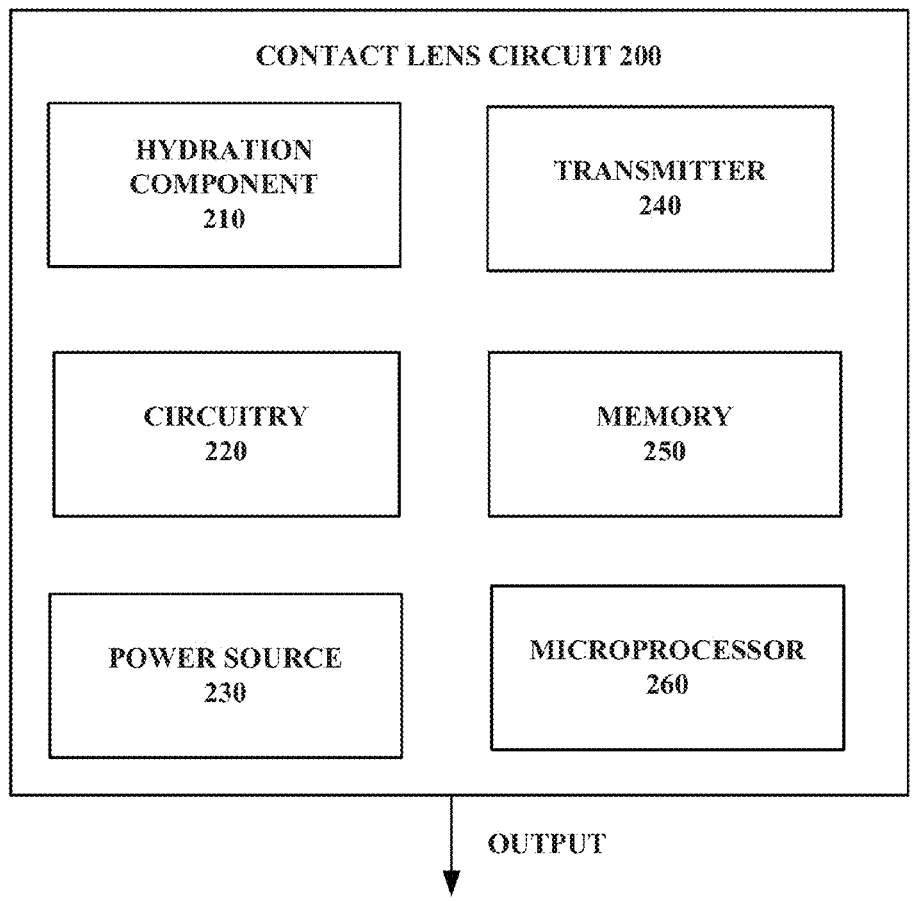
FIG. 2 is an illustration of an example contact lens circuit for a contact lens employing a hydration component to generate information indicative of a hydration level of an eye on/in which the contact lens is worn in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is to be evident, however, that such aspects can be practiced without these specific details. In other instances, structures and devices are shown in block diagram form in order to facilitate describing one or more aspects.

In one or more aspects, the disclosed subject matter relates to a contact lens. The contact lens can include a substrate that forms at least part of a body of the contact lens and a hydration component that generates information associated with a hydration level of an eye on/in which the contact lens is worn. In an aspect, the hydration component applies an electric current to the contact lens and measures conductivity between two points on the contact lens resulting from the electric current to generate information associated with eye hydration level.

In another aspect, a method is disclosed comprising generating information associated with hydration level of an eye in which a contact lens is worn using a hydration component within the contact lens. The method can further include employing the hydration component to apply an electric current to the contact lens, and measuring conductivity between N points (N is an integer greater than 1) on the contact lens resulting from the electric current to generate information associated with hydration level In one or more additional aspects a device is presented comprising an interface component that interfaces with and receives from a contact lens, data relating to hydration level of an eye of a wearer of the contact lens. The device can further include an analysis component that analyzes the received data and determines the eye hydration level, and a display component that generates a display corresponding to the hydration level.

Apparatus, systems, and methods disclosed herein thus relate to a contact lens with means for sensing or generating information indicative of a hydration level of an eye in which the contact lens is worn. In turn, a processor associated with the contact lens can analyze the information and based on the analysis a determination or inference is made regarding eye hydration level. As used herein, hydration level of an eye refers to an amount of tear fluid, including tear film, located on the eye and/or within the eye cavity. The contact lens can further wirelessly transmit information pertaining to the hydration level of the eye to a remote device. In an aspect, the remote device can request eye hydration level information from the contact lens, and the contact lens can generate and send the information in response to the request.

The means for sensing or generating information indicative of eye hydration level by the contact lens can vary. In an aspect, the contact lens can employ a hydration component that can apply various means for generating or sensing the information indicative of eye hydration level. In one aspect, the hydration component can apply an electric current to the contact lens and measure conductivity between two or more points, such as electrodes, on the contact lens to generate a signal corresponding to the conductivity of the contact lens. For example, the hydration component can employ a four point probe to generate sheet resistance information of the contact lens. In another aspect, the hydration component can employ pressure sensors and/or piezoelectric sensors that measure pressure and/or a piezoelectric effect associated with swelling of a substrate of the contact lens to sense eye hydration. For example, the sensors can measure swelling of a hydrogel substrate from which the contact lens. The hydrogel can comprise a network of polymer chains that are hydrophilic and thus absorb tear fluid. Accordingly hydrogel swelling/shrinking information provides an indication of amount of tear fluid absorbed within the hydrogel and thus indirectly relates to eye hydration level.

The hydration component captures information indicative of eye hydration level (e.g. electrical conductivity information, sheet resistance information, and/or swelling information) and generates signals corresponding to the information. In an aspect, the signals generated by the hydration component of the contact lens can be captured by a local integrated circuit and reported out through a radio frequency (RF) interface. The reported signals can further be received at a reader device that analyzes the signals in connection with determining or inferring eye hydration level eye in which the contact lens is worn. In another aspect, signals generated by the hydration component can be captured by a local integrated circuit and analyzed by a microprocessor located on/within the contact lens itself to determine eye hydration level. The determined hydration level can further be reported out via an RF interface.

FIG. 1A is an illustration of an exemplary non-limiting system 100 that includes a contact lens 102 employing a hydration component to generate information indicative of hydration level of an eye in which the contact lens 102 is worn. The system 100 includes a contact lens covering at least a portion of an eye 104 and having a contact lens circuit 106. The contact lens circuit 106 is described in greater detail with reference to FIG. 2. The contact lens circuit 106 can include the hydration component (not shown) to facilitate generating information that can be used to determine hydration level of the eye 104. Information gathered by the hydration component can be captured via the contact lens circuit 106. The hydration component can sense at least characteristics associated with the contact lens that are influenced by amount of tear fluid present within the eye, including but not limited to: conductivity of the contact lens (e.g. in Siemens), sheet resistance of the contact lens (e.g. in Ohms per square), and or swelling of hydrogel from which the contact lens is made.

The contact lens circuit 106 including the hydration component can be located on and/or within a substrate of the contact lens. For example, the contact lens 102 can comprise a hydrogel substrate, such as a silicone hydrogel. One or more electrodes or sensors employed by the hydration component can further be located on and/or within a thickness of the hydrogel.

The hydration component can be integrated physically and/or communicatively with contact lens circuit 106. However, in some aspects, the contact lens circuit 106 can be separated physically and/or communicatively from the hydration component. For example, FIGS. 1B and 1C depict enlarged perspectives of an example contact lens 102 in accordance with aspects described herein. FIG. 1B illustrates a cross-sectional view of contact lens 102 while FIG. 1C depicts a topical/planar view of contact lens 102.

As shown in FIG. 1B, contact lens circuit 106 is located within the substrate (e.g. within the thickness of the hydrogel) of the contact lens 102 and is depicted as a single unit. However, it should be appreciated that contact lens circuit 106 and/or one or more components associated with contact lens circuit 106 can be located on and/or within the substrate. According to this aspect, the contact lens circuit 106 and its associated components, including the hydration component, are co-located and communicatively coupled.

In another embodiment, as seen in FIG. 1C, one or more components of contact lens circuit 106 can be physically dispersed on and/or within the contact lens 102. For example, components of contact lens circuit 106 as presented in FIG. 1C are divided. According to this example, the hydration component can be physically separated from other components of the contact lens circuit. In other aspects, components of the hydration component, such as one or more electrodes and/or one or more sensors, can be physically dispersed on and/or within the contact lens 102 substrate. In any embodiment, one or more components of the contact lens circuit 106, including the hydration component, can be communicatively coupled via one or more wires 112 and/or chemically.

Referring back to FIG. 1A, in some aspects, the contact lens 102 can include one or more components (not shown) to communicate sensed/generated and/or determined information, including but not limited to a signal indicating an output current or voltage associated with conductivity of the contact lens and/or a sheet resistance of the contact lens 102, a signal indicating level of swelling of a hydrogel forming a body of the contact lens, or a determined level of hydration of the eye in which the contact lens is worn. For example, the components can include a radio frequency (RF) antenna in some aspects. In some aspects, the information 108 can be communicated to a reader 110. In some aspects, the reader 110 can be an RF reader. Accordingly, the contact lens 102 can wirelessly communicate with reader 110.

Figure 3:
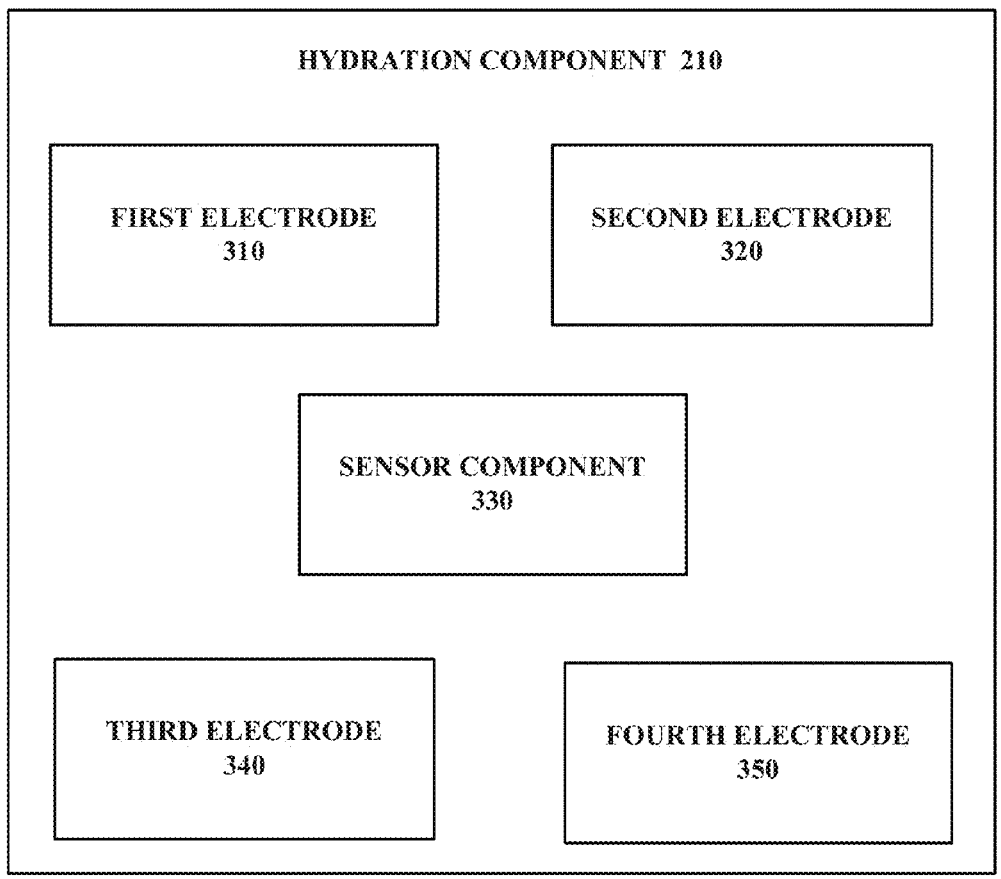
FIG. 3 is an is an illustration of an example hydration component that generates information indicative of a hydration level of an eye in accordance with aspects described herein.

FIG. 2 is an illustration of a contact lens circuit for a contact lens employing a hydration component 210 in accordance with aspects described herein. FIG. 3 is an illustration of hydration component 210 in accordance with aspects described herein. In various aspects, the contact lens circuit 200 can include one or more of the structure and/or functionality of the contact lens circuit 106 (and vice versa).

As shown in FIG. 2, the contact lens circuit 200 can include a hydration component 210, circuitry 220, power source 230, transmitter 240, memory 250 and/or microprocessor 260. In some aspects and as shown in FIG. 2, the contact lens circuit 200 includes hydration component 210 and its associated components. In other aspects, hydration component 210 can be physically and/or communicatively independent (not shown) from contact lens circuit 200. However, in embodiments, one or more of the hydration component 210, its associated components, circuitry 220, power source 230, transmitter 240, memory 250 and/or microprocessor 260, can be communicatively coupled to one another to perform one or more functions of contact lens circuit 200.

With reference to FIG. 3, the hydration component 210 can employ various means for generating/sensing information indicative of hydration level of an eye in which the contact lens employing contact lens circuit 200, is worn. In an aspect, the hydration component 210 measures conductivity or resistivity of the contact lens by employing two or more electrodes, (e.g. first electrode 310, second electrode 320, third electrode 340, fourth electrode 350, and etc.) that are located on and/or within a hydrogel body of the contact lens. For example, the hydration component 210 can measure intensity of current generated between two or more points (e.g. two electrodes), located on and/or within the substrate in response to an applied voltage. In another example, the hydration component 210 can apply a constant current between electrodes and measure change in potential at one of the electrodes. According to this aspect, conductivity and/or resistivity of the contact lens will vary depending on amount of tear fluid present on and/or within the contact lens. Such variance in conductivity/resistivity of the contact lens can be compared to a known base conductivity/resistivity level of the contact lens to equate hydration level of the eye in which the contact lens is worn.

In another aspect, the hydration component 210 can measure sheet resistance of the contact lens (e.g. via two-terminal, three terminal, or M terminal sensing (M is an integer)). For example, the hydration component 210 can use four electrodes (e.g. first electrode 310, second electrode 320, third electrode 340, and fourth electrode 350), as a four point probe. A four point probe is used to avoid contact resistance, which can often be of same magnitude as the sheet resistance. In an aspect, the hydration component 210 applies a constant current to two probes (e.g. first electrode 310 and second electrode 320) and measures potential on the other two probes (e.g. third electrode 340 and fourth electrode 350). In order to facilitate calculating sheet resistance of the contact lens (e.g. via microprocessor 260 and/or an external processor), geometrical locations and relative geometric shape resulting from the geometrical locations of each of the respective electrodes with respect to the contact lens are preferably known. For example, for electrodes can be dispersed in a substantially straight line with substantially equal or know spacing there between.

It should be appreciated that the two or more electrodes employed by hydration component 210, such as electrodes 310, 320, 340, 350, can be integrated at various locations on and/or within the substrate of the contact lens. For example, electrodes may be provided on opposing surfaces of the contact lens. According to this example, a first electrode 310 may be provided on an inner surface of the contact lens, (where the inner surface of the contact lens is the surface of the contact lens touching the eyeball when the contact lens is inserted into the eye) while a second electrode 320 may be provided on an outer surface of the contact lens (where the outer surface of the contact lens is the surface of the contact lens opposite the inner surface and facing the external environment). In another example, respective electrodes may be located on opposing radial sides of the contact lens and within the thickness of the substrate of the contact lens.

In addition to or in the alternative of employing the electrode conductivity and sheet resistance sensing means discussed above, the hydration component 210 can employ sensor component 330 to sense properties indicative of hydration level of an eye in which the contact lens is worn. Sensor component 330 can include one or more sensors configured to sense swelling of the hydrogel substrate of the contact lens. The one or more sensors can be located on and/or within the hydrogel substrate. For instance, as the hydrogel substrate of the contact lens absorbs tear fluid, it will swell. Similarly, as the hydrogel substrate of the contact lens becomes less hydrated, it will shrink.

In an aspect, the one or more sensors include a pressure sensor. In another aspect, the one or more sensors include a piezoelectric sensor. In an embodiment, the hydration component 210 measures pressure within the contact lens and/or a piezoelectric effect within the contact lens in response to swelling or shrinking (e.g. in thickness) of the hydrogel substrate from which the contact lens is made. In an aspect, the hydration component 210 measures pressure of the hydrogel with respect to two sensors where the hydrogel is sandwiched between the two sensors. It should be appreciated that depending on whether the hydrogel is swelling or shrinking as well as location, type and integration manner of a sensor on/within the hydrogel, force sensed by the sensor will vary. For example, in some instances, swelling or shrinking of the hydrogel will cause a pressing force on one or more sensors provided on/within the hydrogel. In other instances, swelling or shrinking of the hydrogel will cause a pulling force on one or more sensors provided on/within the hydrogel. Accordingly, a decrease in hydration level of an eye may be associated with either an increase or decrease in pressure against a sensor employed by the hydration component 210.

Referring back to FIG. 2, in some aspects, the contact lens circuit 200 can further include circuitry 220, power source 230, transmitter 240, memory 250 and/or microprocessor 260. In particular, the hydration component 210 senses/generates information relating to hydration level of the eye in which a contact lens is worn. For example, such information includes measured conductivity of the contact lens, sheet resistance of the contact lens, and or pressure or piezoelectric effect on/within the contact lens. The hydration component 210 can further generate signals representative of sensed/generated information. Circuitry 210 facilitates collection of signals generated by the hydration component 210. In some aspects, circuitry 210 further facilitates processing of signal received from the hydration component. Circuitry 220 can further send received signals to transmitter 220, memory 250, and/or microprocessor 260. Power source 230 can include any suitable power source, (e.g. a battery or solar power source), that can provide necessary power for the operation of the various component of the contact lens circuit 200. For example, power source 230 can provide voltage or current for generating conductivity/resistivity information and/or sheet resistance information of the contact lens via the hydration component 210.

In an aspect, transmitter 240 transmits sensed/generated information indicative of a hydration level of an eye in which the contact lens is worn (e.g. contact lens resistivity and/or conductivity information, contact lens sheet resistance information, and/or hydrogel swelling information) to a reader device remote from the contact lens. For example, the transmitter 240 may include an RF antenna in some aspects. In turn, the reader device may perform analysis and processing of the sensed/generated information indicative of a hydration level of an eye in which the contact lens is worn. In other aspects, the microprocessor 260 can receive information from the hydration component 210 indicative of a hydration level of an eye in which the contact lens is worn (e.g. contact lens resistivity and/or conductivity information, contact lens sheet resistance information, and/or hydrogel swelling information). The microprocessor 260 can further perform analysis and processing of the sensed/generated information.

Memory 250 can store information sensed/generated by the hydration component 210 (e.g. contact lens resistivity and/or conductivity information, contact lens sheet resistance information, and/or hydrogel swelling information). Memory 250 may also store information relating contact lens resistivity and/or conductivity information, contact lens sheet resistance information, and/or hydrogel swelling information to eye hydration levels. Further, memory 250 can store information necessary for microprocessor 260 to perform calculations and determinations of contact lens conductivity, contact lens resistivity, contact lens sheet resistance, and hydrogel swelling. For example, memory 250 can store algorithms and known values required for the algorithmic calculations (e.g. base values of the contact lens conductivity, contact lens resistivity, contact lens sheet resistance, hydrogel thickness, electrode potentials, and applied current values, geometric configuration and spacing of the electrodes, and etc.). Memory 250 can further store computer-executable instructions for execution by the microprocessor 260. The microprocessor 260 can execute computer-executable instructions to perform one or more functions of the contact lens circuit 200.

Microprocessor 260 can perform a variety of functions to conduct analysis and processing of information sensed/generated by the hydration component 210 to determine eye hydration level of a wearer of the contact lens. In an aspect, the microprocessor 260 can employ any suitable information sensed/generated by hydration component 210. For example, microprocessor 260 can employ combined contact lens resistivity and/or conductivity information, contact lens sheet resistance information, and/or hydrogel swelling information, to determine hydration level of an eye. In an aspect, the microprocessor can employ a look up table in memory 250 relating to information sensed/generated by the hydration component 210 to an output value associated with eye hydration level. In another aspect, the microprocessor 260 can employ various algorithms relating information sensed/generated by the hydration component 210 to an output value of an eye hydration level. For example, the microprocessor can determine sheet resistance of the contact lens based on sensed conductivity values from a multi-point probe employed by the hydration component 210 and in turn relate the determined sheet resistance to an eye hydration level using various algorithms or a look up table stored in memory 250. In another example the microprocessor 260 can convert an output current signal relating to a resistivity or conductivity of the contact lens to an eye hydration level. In turn, the transmitter 240 can transmit the determined eye hydration level information to a reader device.

In an embodiment, microprocessor can implement various classification (explicitly or implicitly trained) schemes or systems (e.g., support vector machines, neural networks, expert systems, Bayesian belief networks, fuzzy logic, data fusion engines, etc.) in connection with performing analysis of sensed/generated information. A classifier can map an input attribute vector, $x=(x1, x2, x3, x4, xn)$, to a confidence that the input belongs to a class, such as by $f(x)=confidence(class)$. Such classification can employ a probabilistic or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

In an aspect, the hydration component 210 performs sensing/generating of eye hydration level information on a continuous basis. For example, the hydration component 210 can perform sensing/generating of eye hydration level information according to a programmed schedule, such as every minute, every thirty minutes, every hour and etc. Memory 250 and microprocessor 260 can facilitate directing and controlling sensing/generating by hydration component 210. According to this aspect, transmitter 240 can further be configured to transmit sensed/generated information according to a same or similar programmed schedule as the hydration component 210. In another aspect, where microprocessor 260 analyzes sensed/generated information to determine an eye hydration level, the transmitter 240 can be configured to transmit determined eye hydration levels in response to the eye hydration level being below a predetermined threshold. For example, the hydration component 210 may routinely sense/generate information indicative of an eye hydration level and the microprocessor may routinely determine the eye hydration level based on the sensed/generated information. When the eye hydration level falls below a predetermined threshold, the transmitter 240 can send an alert to a reader device.

In another aspect, the hydration component 210 can perform sensing/generating of eye hydration level information in response to a request signal. For example, transmitter 240 can receive a request from a remote device for eye hydration level information. In turn, the hydration component 210 can sense/generate information indicative of eye hydration level information and the microprocessor can further determine or infer eye hydration level based on the sensed/generated information. The transmitter 240 can transmit sensed/generated and/or determined/inferred eye hydration level information back to the reader device.

With reference now to FIGS. 4A, 4B and 4C, FIGS. 4A and 4B depict different perspectives of an example contact lens having a four point detection probe for generating information indicative of a hydration level of an eye on/in which the contact lens is worn in accordance with aspects described herein. FIG. 4C illustrates an example contact lens having sensors for sensing information indicative of a hydration level of an eye on/in which the contact lens is worn in accordance with aspects described herein.

Turning initially to FIG. 4A, presented is a cross section of an example contact lens 410 comprising a four-point probe integrated therein to serve as the contact lens hydration component (e.g. hydration component 210). The multi-point probe of this example includes four sensors 402, 404, 406, and 408 that are configured to receive an applied voltage and generate a detectable potential value that can be analyzed to determine sheet resistance of the contact lens. It is to be appreciated that any suitable number of problems is contemplated and intended to fall within the scope of there herein claims. The sheet resistance of the contact lens can further be employed to determine hydration level of the contact lens. The location and spacing of the four probes/electrodes can be mapped in an associated memory (e.g. memory 250). Contact lens 410 further includes circuitry 106. Circuitry 106 can include one or more of the structure and/or functionality of the contact lens circuit 200 (and vice versa). Some or all of the fourth probes 402, 404, 406, and 408 can be electrically connected to one another and/or electrically connected to circuitry 106 (e.g. via one or more wires).

As seen in FIG. 4A the four probes 402, 404, 406, and 408 are located within the substrate of the contact lens 410 an within a substantially straight line with respect to one another. The probes are further dispersed so as to not overlap with the center of the contact lens 410 at which the iris/pupil of the eye is adjacent to when the lens is placed over the eye 104. However, the location of the probes depicted in FIG. 4A is merely demonstrative. The probes 402, 404, 406, and 408 may be located at various positions on/or within the substrate. For example, in an aspect, the probes 402, 404, 406, and 408 can be located on the outer surface 412 or inner surface of the contact lens and inside or outside of the substrate.

FIG. 4B presents a top planar view of an example contact lens 410 comprising a four-point probe integrated therein to serve as the contact lens hydration component (e.g. hydration component 210). The four point probe comprises electrodes 402, 404, 406 and 408. The electrodes can be located at various locations of the contact lens 420. As seen in FIG. 4B, the probes 402 and 404 are electrically connected via a wire 416, and probes 406 and 408 are electrically connected via a wire 416. Each pair of probes 402-404 and 406-408 can further be connected to circuit 106 via wire 416.

FIG. 4C depicts cross-sectional views of a hydrated contact lens 420 and a dehydrated contact lens 430, each having two pressure sensors 422 and 424 integrated therein. Contact lens 420 and contact lens 430 have a first sensor 424 provided on an outer surface of the contact lens and a second sensor 422 provided on an inner surface of the contact lens. However, it should be appreciated that location of the sensors can vary. For example sensor 422 and 424 can be located within the substrate and not against a surface of the contact lens. Further, although two sensors are depicted in contact lenses 420 and 430, it should be appreciated that any suitable number sensors can be employed by a contact lens as the contact lens hydration component (e.g. hydration component 210).

The sensors 422 and 424 can further be connected to each other and/or circuit 106 via one or more wires. In an aspect, contact lens 420 is hydrated/filled with tear fluid and thus swollen. For example contact lens 420 can represent a contact lens that has been recently provided within an eye. On the other hand, contact lens 430 depicts a contact lens that has been shrunk as a result of depletion of tear fluid therein. For example, contact lens 430 can represent a contact lens that is worn over a period of time in a dehydrated eye. In an aspect, the pressure between sensors 424 and 422 of contact lens 420 is greater than the pressure against sensors 424 and 422 of contact lens 430 as a result of the swelling of the contact lens 420 and/or the shrinking of contact lens 430. According to this aspect, the lower pressure against contact lenses 424 and 422 of contact lens 430 can be indicative of a low hydration level of the eye 104 in which the contact lens 430 is worn.

Figure 5:
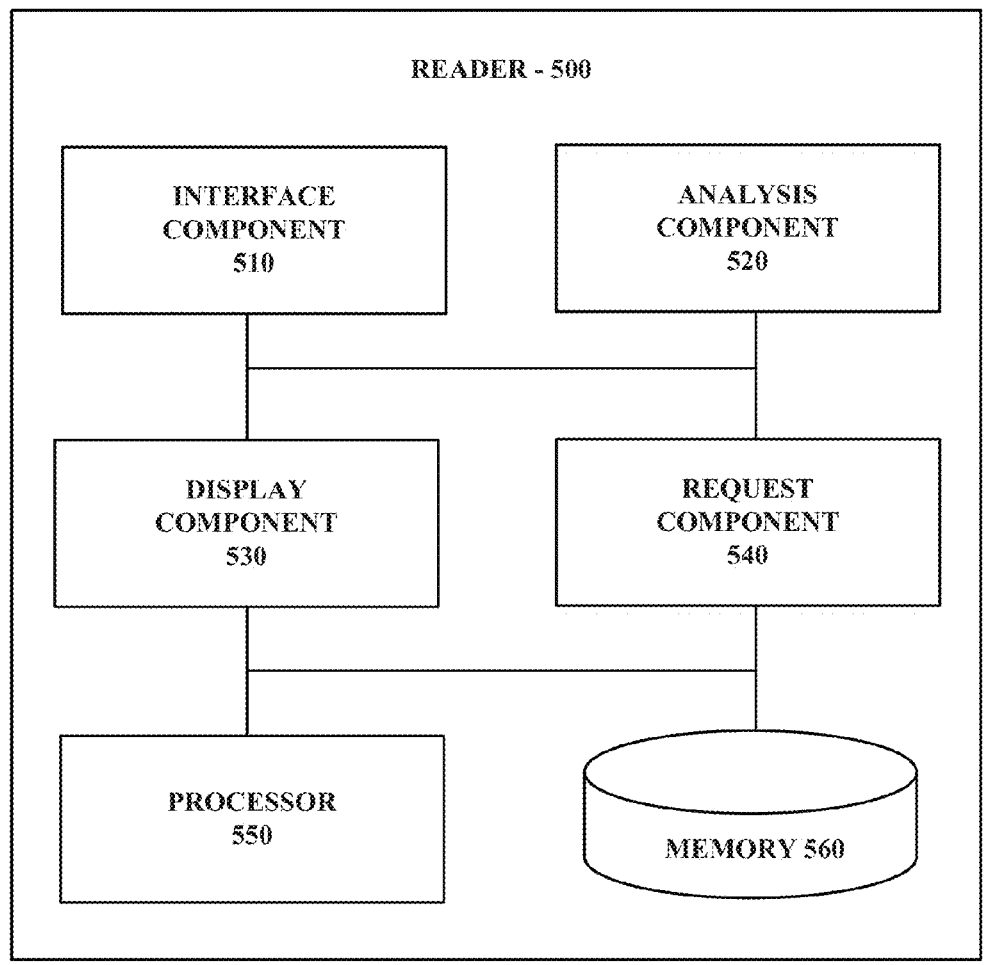
FIG. 5 is an illustration of an exemplary non-limiting reader device that receives from a contact lens, information indicative of a hydration level of an eye on/in which the contact lens is worn in accordance with aspects described herein.

FIG. 5 is an illustration of an exemplary non-limiting reader device 500 that interfaces with a contact lens employing a hydration component to receive information associated with hydration level of an eye in which the contact lens is worn in accordance with aspects described herein. In various aspects, the reader device 500 can include one or more of the structure and/or functionality of the reader device 110 (and vice versa).

As shown in FIG. 5, reader device 500 can include interface component 510, analysis component 520, display component 530, and request component 540. In an embodiment, aspects of device 500 constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described. Device 500 can include memory 560 for storing computer executable components and instructions. A processor 550 can facilitate operation of the computer executable components and instructions by device 500.

Interface component 510 interfaces with and receives from at least one contact lens, data relating an eye hydration level. In particular, interface component 510 can interface with contact lenses described herein that comprise a contact lens circuit such as contact lens circuit 106 and/or contact lens circuit 200. In an aspect, interface component 510 employs a receiver, such as an RF receiver, to receive sensed/generated and/or determined information from a contact lens comprising a contact lens circuit as described herein. In some aspects, interfacing component 510 can receive from a contact lens, a determined value indicating a hydration level of an eye in which the contact lens is worn. According to this aspect, the contact lens may include appropriate circuitry and components to process data provided by a hydration component thereon and/or therein.

In another aspect, the reader can receive raw data from a contact lens that is indicative of eye hydration levels. For example, the interface component 510 may receive contact lens resistivity and/or conductivity information, contact lens sheet resistance information, and/or hydrogel swelling/shrinking information that is sensed/generated by a hydration component located within the contact lens. According to this embodiment, the reader 500 can comprise an analysis component 520 that can analyze the received raw data and to determine a hydration level of an eye in which the contact lens sending the information, is worn. In an aspect, the analysis component 520 can perform the same or similar analysis techniques as microprocessor 260. In particular, the analysis component 520 can employ any received information to determine a hydration level of an eye. For example, the analysis component 520 can employ combined contact lens resistivity and/or conductivity information, contact lens sheet resistance information, and/or hydrogel swelling information, to determine a hydration level of an eye. The analysis component 520 can further employ information in memory 340 that relates the received information to an eye hydration level. The analysis component 520 may employ various look up tables, algorithms, and/or classifiers relating sensed/generated information to an eye hydration level.

According to this aspect, memory 560 can store information relating contact lens resistivity and/or conductivity information, contact lens sheet resistance information, and/or hydrogel swelling information to eye hydration levels. Further, memory 360 can store information necessary for analysis component 520 to perform calculations and determinations of contact lens conductivity, contact lens resistivity, contact lens sheet resistance, and hydrogel swelling. For example, memory 560 can store algorithms and known values required for the algorithmic calculations (e.g. base values of the contact lens conductivity, the contact lens resistivity, the contact lens sheet resistance, the hydrogel thickness, electrode potentials, and applied current values, the geometric configuration of the electrodes, and etc.).

Request component 540 can transmit a request to a contact lens for data relating to a hydration level of an eye in which the contact lens is worn. For example, the request component can request an eye hydration level of an eye in which the contact lens is worn and/or sensed/detected information indicative of an eye hydration level. In an aspect, the request can prompt the contact lens to perform sensing/generation and/or analysis of eye hydration level information.

The reader device 500 can further include a display component 530 that generates a display corresponding to a hydration level of an eye in which a contact lens as described herein, is worn. Reader device 500 can include any suitable computing device capable of wirelessly transmitting and receiving information, displaying information, and/or processing eye hydration level information. For example, reader device 500 can include but is not limited to, a cellular phone, a smart phone, a personal digital assistant, a tablet PC, a laptop computer, or a desktop computer.

Figure 6:
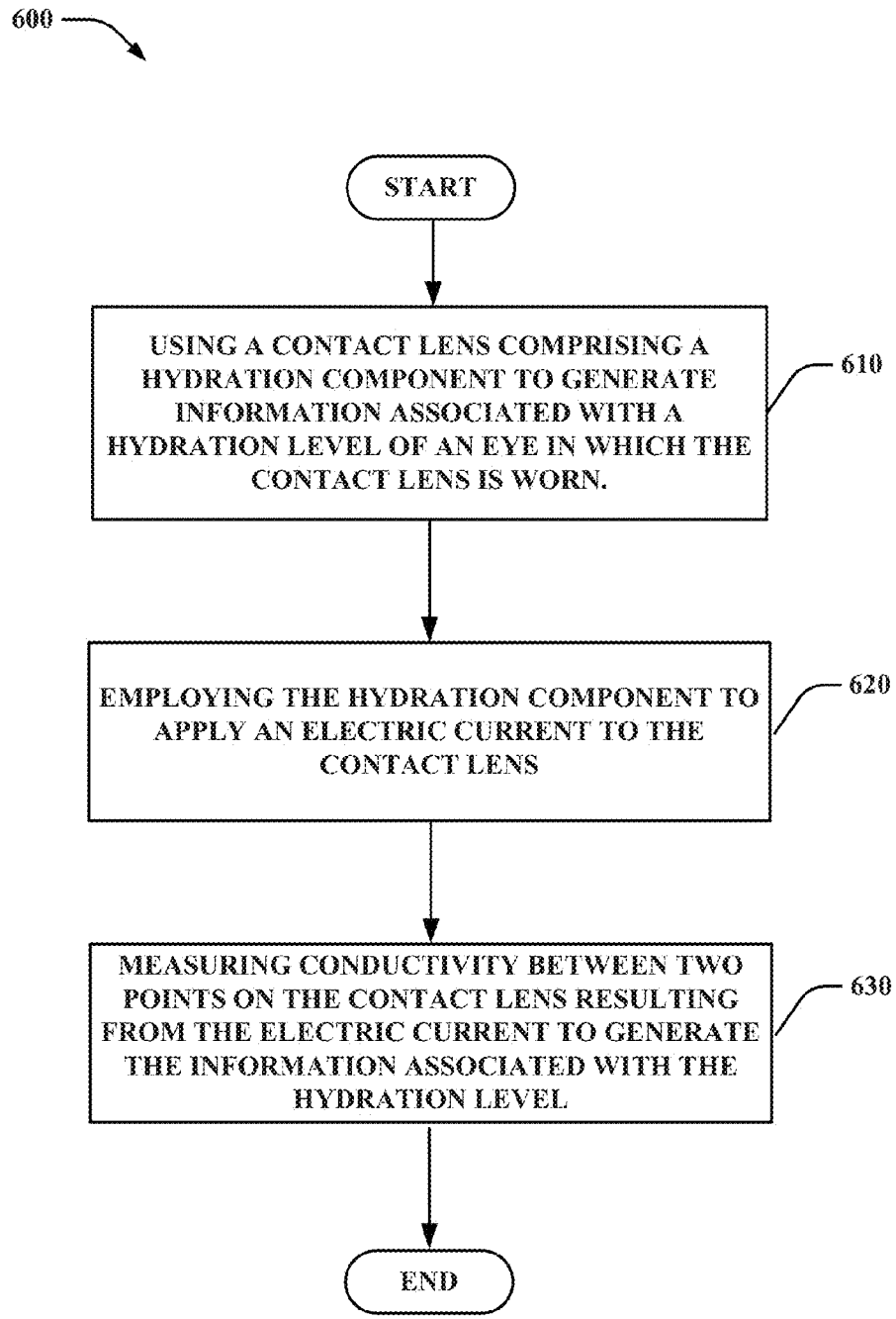
FIG. 6 is an exemplary flow diagram of a method that facilitates employing a contact lens to generate information indicative of a hydration level of an eye on/in which the contact lens is worn in accordance with aspects described herein.
Figure 7:
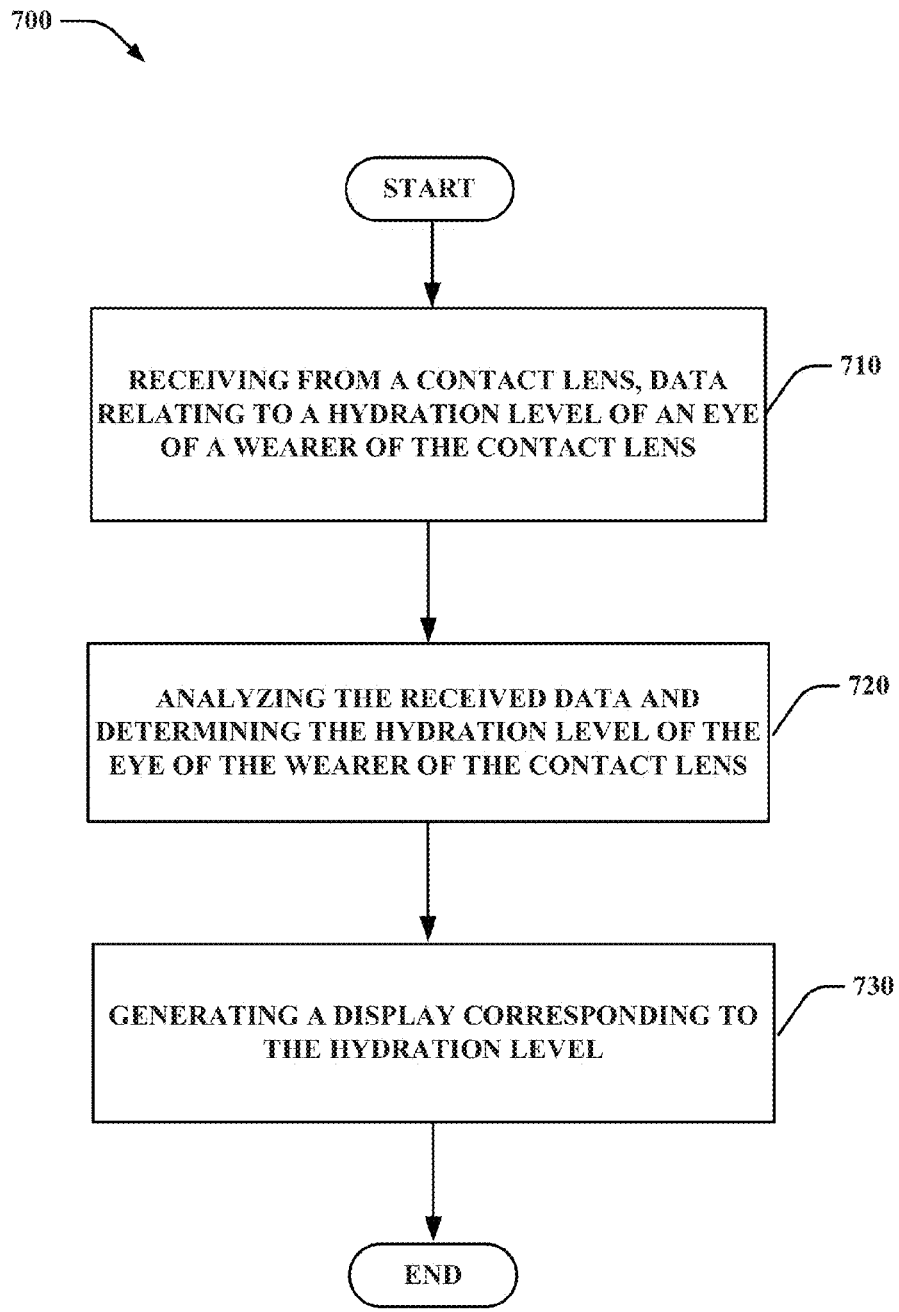
FIG. 7 is an exemplary flow diagram of a method that facilitates receiving from a contact lens, information indicative of a hydration level of an eye on/in which the contact lens is worn in accordance with aspects described herein.

FIGS. 6-7 illustrates methodologies or flow diagrams in accordance with certain aspects of this disclosure. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Referring now to FIG. 6, presented is a flow diagram of an example application of systems and apparatuses disclosed in this description in accordance with an embodiment. In an aspect, in exemplary methodology 600, a contact lens such as those described herein (e.g. 102 and the like) is employed to generate information pertaining to a hydration level of an eye in which the contact lens is worn. At 610, a contact lens comprising a hydration level hydration component (e.g. contact lens 102) is used to generate information associated with a hydration level of an eye in which the contact lens is worn, (e.g. using hydration component 210). At 620, the hydration level hydration component is employed to apply an electric current to the contact lens. Then at 630, the conductivity between two points on the contact lens resulting from the electric current is measured to determine the information associated with the hydration level (e.g. using the hydration component 210).

Turning now to FIG. 7, a method 700 can include receiving information generated by a contact lens relating to an eye hydration level of the wearer of the contact lens (e.g. using reader device 110 or 500). At 710 data relating to a hydration level of an eye of a wearer of the contact lens is received from the contact lens (e.g. using interface component 510). At 720, the received data is analyzed and the blood alcohol level of the wearer of the contact lens is hydration level of the eye of the wearer of the contact lens is determined (e.g. using analysis component 520). At 730, a display is generated corresponding to the hydration level (e.g. using display component 530).

Exemplary Networked and Distributed Environments

Figure 8:
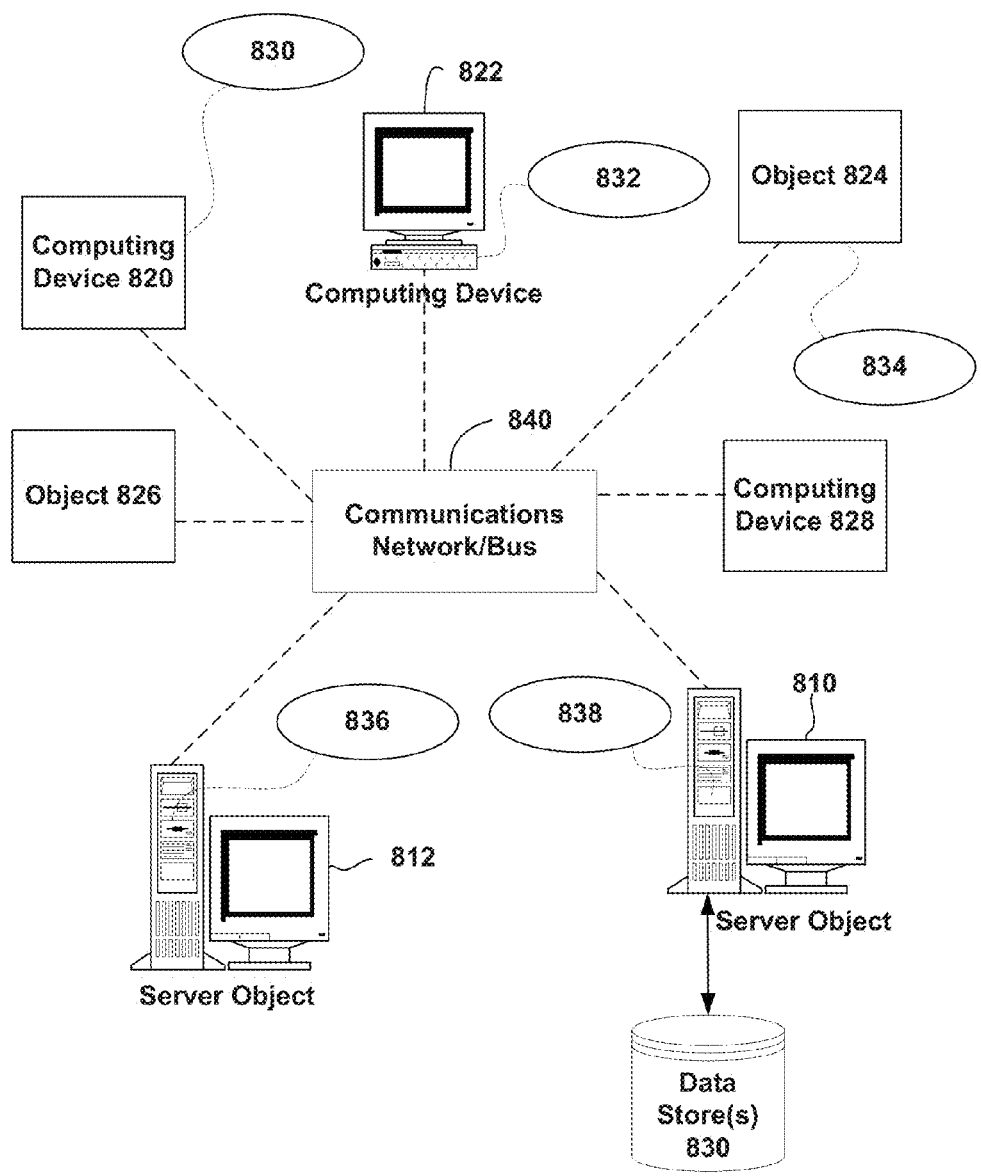
FIG. 8 is an illustration of a schematic diagram of an exemplary networked or distributed computing environment with which one or more aspects described herein can be associated.

FIG. 8 provides a schematic diagram of an exemplary networked or distributed computing environment with which one or more aspects described in this disclosure can be associated. The distributed computing environment includes computing objects 810, 812, etc. and computing objects or devices 820, 822, 824, 826, 828, etc., which can include programs, methods, data stores, programmable logic, etc., as represented by applications 830, 832, 834, 836, 838. It can be appreciated that computing objects 810, 812, etc. and computing objects or devices 820, 822, 824, 826, 828, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 810, 812, etc. and computing objects or devices 820, 822, 824, 826, 828, etc. can communicate with one or more other computing objects 810, 812, etc. and computing objects or devices 820, 822, 824, 826, 828, etc. by way of the communications network 840, either directly or indirectly. Even though illustrated as a single element in FIG. 8, network 840 can include other computing objects and computing devices that provide services to the system of FIG. 8, and/or can represent multiple interconnected networks, which are not shown.

In a network environment in which the communications network/bus 840 can be the Internet, the computing objects 810, 812, etc. can be Web servers, file servers, media servers, etc. with which the client computing objects or devices 820, 822, 824, 826, 828, etc. communicate via any of a number of known protocols, such as the hypertext transfer protocol (HTTP).

Exemplary Computing Device

As mentioned, advantageously, the techniques described in this disclosure can be associated with any suitable device. It is to be understood, therefore, that handheld, portable and other computing devices (including active contact lens having circuitry or components that compute and/or perform various functions). As described, in some aspects, the device can be the contact lens (or components of the contact lens) and/or the reader described herein. In various aspects, the data store can include or be included within, any of the memory described herein, any of the contact lenses described herein and/or the reader devices described herein. In various aspects, the data store can be any repository for storing information transmitted to or received from the contact lens.

Figure 9:
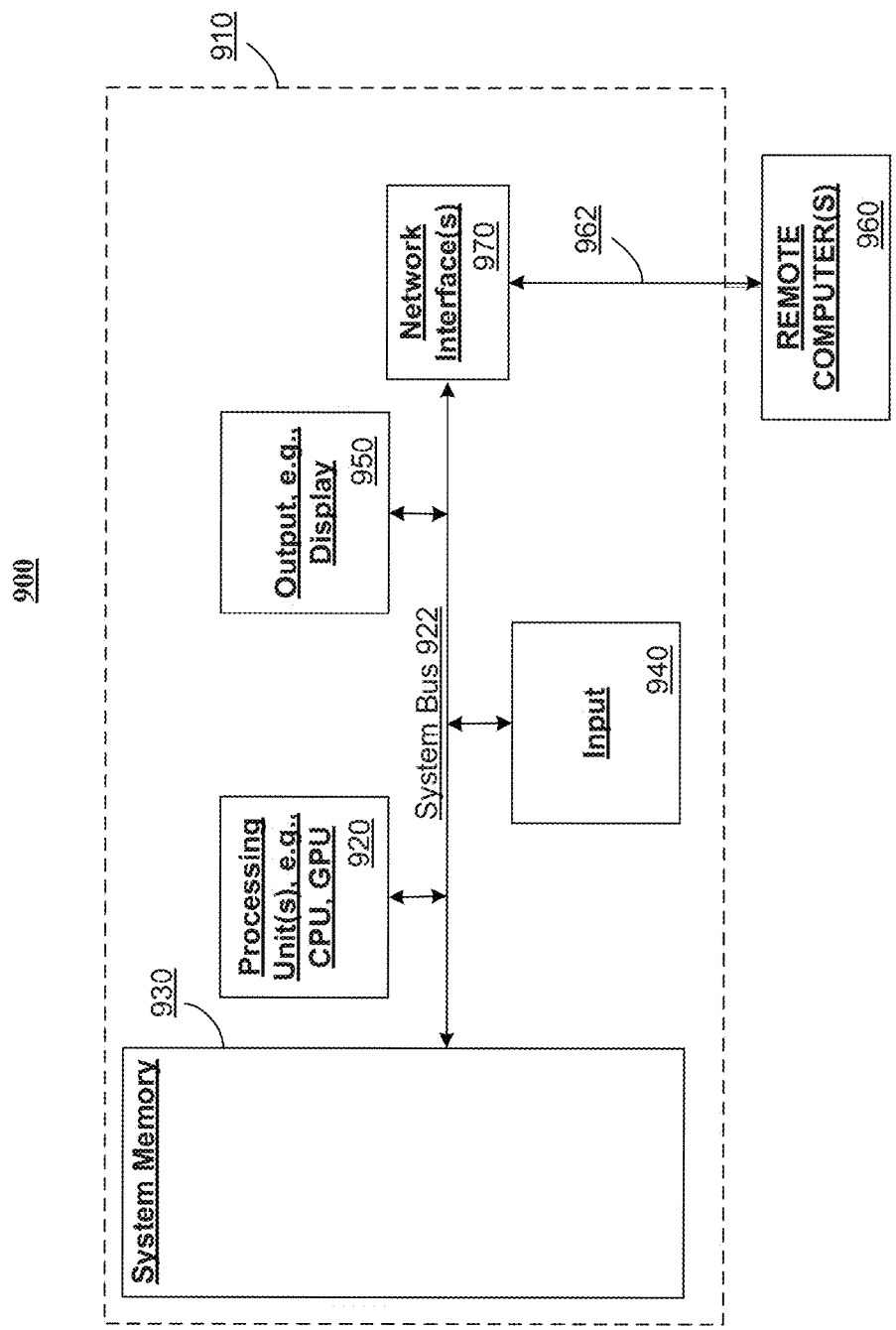
FIG. 9 is an illustration of a schematic diagram of an exemplary computing environment with which one or more aspects described herein can be associated.

FIG. 9 illustrates an example of a suitable computing system environment 900 in which one or aspects of the aspects described in this disclosure can be implemented. Components of computer 910 can include, but are not limited to, a processing unit 920, a system memory 930, and a system bus 922 that couples various system components including the system memory to the processing unit 920.

Computer 910 typically includes a variety of computer readable media and can be any available media that can be accessed by computer 910. The system memory 930 can include computer storage media in the form of volatile and/or nonvolatile memory such as read only memory (ROM) and/or random access memory (RAM). By way of example, and not limitation, memory 930 can also include an operating system, application programs, other program components, and program data.

A user can enter commands and information into the computer 910 through input devices 940 (e.g., keyboard, keypad, a pointing device, a mouse, stylus, touchpad, touch screen, motion detector, camera, microphone or any other device that allows the user to interact with the computer 910). A monitor or other type of display device can be also connected to the system bus 922 via an interface, such as output interface 950. In addition to a monitor, computers can also include other peripheral output devices such as speakers and a printer, which can be connected through output interface 950.

The computer 910 can operate in a networked or distributed environment using logical connections to one or more other remote computers, such as remote computer 960. The remote computer 960 can be a personal computer, a server, a router, a network PC, a peer device or other common network node, or any other remote media consumption or transmission device, and can include any or all of the elements described above relative to the computer 910. The logical connections depicted in FIG. 9 include a network 970, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and nonvolatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art. Furthermore, it is to be appreciated that components, devices, systems, circuits, etc. described in the disclosure can be configured to perform as well as actually perform the functionalities respectively associated therewith.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating therefrom. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
   a substrate that forms at least part of a body of the contact lens, wherein the substrate comprises a hydrogel; and
   a hydration component that is configured to generate information associated with a hydration level of an eye in which the contact lens is worn, wherein the hydration component comprises one or more sensors to generate the information associated with the hydration level, and wherein the one or more sensors include at least one sensor configured to sense swelling of the hydrogel.

2. The contact lens of claim 1, wherein the at least one sensor is a pressure sensor that is configured to measure pressure associated with swelling of the hydrogel.

3. The contact lens of claim 1, wherein the at least one sensor is a piezoelectric sensor that is configured to measure a piezoelectric effect resulting from pressure associated with swelling of the hydrogel.

4. The contact lens of claim 1, further comprising:
   a circuit disposed on or within the substrate that is configured to receive the information associated with the hydration level; and
   a transmitter that is configured to transmit the information associated with the hydration level.

5. The contact lens of claim 4, wherein the transmitter is configured to transmit the information associated with the hydration level in response to a request.

6. The contact lens of claim 4, further comprising a processor that is configured to determine hydration level of the eye in which the contact lens is worn based on the information.

7. The contact lens of claim 6, wherein the processor is configured to determine the hydration level in response to a request and wherein the transmitter is configured to transmit data indicating the hydration level in response to the request.

8. The contact lens of claim 6, wherein the transmitter is configured to transmit the information associated with the hydration level in response to a determination that the hydration level is below a predetermined threshold.

9. The contact lens of claim 6, wherein the processor is configured to periodically determine the hydration level based on a programmed schedule.

10. A method comprising:
generating information associated with a hydration level of an eye in which a contact lens is worn using a hydration component within the contact lens, wherein the hydration component uses one or more sensors to generate the information associated with the hydration level, and wherein the one or more sensors include at least one sensor configured to sense swelling of a hydro gel in the contact lens.

11. The method of claim 10, wherein the at least one sensor is a pressure sensor that measures pressure associated with swelling of the hydrogel.

12. The method of claim 10, wherein the at least one sensor is a piezoelectric sensor that measures a piezoelectric effect resulting from pressure associated with swelling of the hydrogel.

13. The method of claim 10, further comprising:
receiving the information via a circuit disposed on or within the contact lens; and
transmitting the information to a device remote from the contact lens.

14. The method of claim 13, wherein the transmitting the information comprises transmitting the information in response to a request from the remote device.

15. The contact lens of claim 13, further comprising determining the hydration level of the eye in which the contact lens is worn based on the information.

16. The method of claim 15, wherein the transmitting the information comprises transmitting the information in response to determining that the hydration level is below a predetermined threshold.

17. The contact lens of claim 15, wherein the determining the information comprises determining the information routinely according to a programmed schedule.

18. A contact lens, comprising:
a substrate that forms at least part of a body of the contact lens; and
a hydration component that is configured to generate information associated with a hydration level of an eye in which the contact lens is worn, wherein the hydration component is configured to apply an electric current to the contact lens and measure sheet resistance of the contact lens using a four-point probe located on or within the contact lens to generate the information associated with the hydration level.

19. The contact lens of claim 18, further comprising:
a circuit disposed on or within the substrate that is configured to receive the information associated with the hydration level; and
a transmitter that is configured to transmit the information associated with the hydration level.

20. The contact lens of claim 19, wherein the transmitter is configured to transmit the information associated with the hydration level in response to a request.

21. The contact lens of claim 19, further comprising a processor that is configured to determine hydration level of the eye in which the contact lens is worn based on the information.

22. The contact lens of claim 21, wherein the processor is configured to determine the hydration level in response to a request and wherein the transmitter is configured to transmit data indicating the hydration level in response to the request.

23. The contact lens of claim 21, wherein the transmitter is configured to transmit the information associated with the hydration level in response to a determination that the hydration level is below a predetermined threshold.

24. The contact lens of claim 21, wherein the processor is configured to periodically determine the hydration level based on a programmed schedule.

* * * * *

UNITED STATES PATENT AND TRADEMARK OFFICE
CERTIFICATE OF CORRECTION

PATENT NO. : 8,989,834 B2
APPLICATION NO. : 13/626603
DATED : March 24, 2015
INVENTOR(S) : Harvey Ho and Babak Amirparviz Page 1 of 1

It is certified that error appears in the above-identified patent and that said Letters Patent is hereby corrected as shown below:

In the Claims,

Claim 10, Column 15, line 24, replace "hydro gel" with "hydrogel"

Signed and Sealed this
Eighteenth Day of August, 2015

Michelle K. Lee
*Director of the United States Patent and Trademark Office*